United States Patent [19]

Marzouk et al.

[11] Patent Number: 6,111,136
[45] Date of Patent: Aug. 29, 2000

[54] METHOD FOR PREPARATION OF PERFLUOROALCANECARBOXYLIC AND PERFLUOROALKANESULFONIC ACIDS

[75] Inventors: Hatem Marzouk, Avon; Laurent Petit, Fontainebleau; Marc Tordeux, Sceaux; Amaya Berecibar, Antony; Claude Wakselman, Paris, all of France

[73] Assignees: Electricite de France Service National; Centre National de la Recherche Scientifique, both of Paris, France

[21] Appl. No.: 09/101,247

[22] PCT Filed: Dec. 24, 1996

[86] PCT No.: PCT/FR96/02079

§ 371 Date: Sep. 4, 1998

§ 102(e) Date: Sep. 4, 1998

[87] PCT Pub. No.: WO97/24309

PCT Pub. Date: Jul. 10, 1997

[30] Foreign Application Priority Data

Dec. 27, 1995 [FR] France .................................. 95 15558

[51] Int. Cl.⁷ .................................................. C07C 309/00

[52] U.S. Cl. ........................... 562/113; 562/125; 562/523; 562/524

[58] Field of Search ..................................... 562/113, 523, 562/524, 125

[56] References Cited

U.S. PATENT DOCUMENTS

| | | | |
|---|---|---|---|
| 4,138,417 | 2/1979 | Ukihashi et al. | 554/133 |
| 4,239,696 | 12/1980 | Schreyer et al. | 562/118 |
| 4,324,741 | 4/1982 | Umemoto et al. | 562/113 |
| 4,784,809 | 11/1988 | Goldbaum et al. | 562/113 |
| 4,866,190 | 9/1989 | Tordeux et al. | 556/111 |
| 4,925,975 | 5/1990 | Aramaki et al. | 562/113 |
| 5,059,711 | 10/1991 | Bielefeldt et al. | 562/113 |

*Primary Examiner*—Gary Geist
*Assistant Examiner*—Taylor V Oh
*Attorney, Agent, or Firm*—Jones & Askew, LLP

[57] ABSTRACT

The invention consists of a new method for preparing perfluoroalcanecarboxylic and perfluoroalcanesulfonic acids in which ozone is made to react, in a protic environment, upon a perfluoroalkyl chain comprising at least one oxydizable chemical group.

18 Claims, No Drawings

METHOD FOR PREPARATION OF PERFLUOROALCANECARBOXYLIC AND PERFLUOROALKANESULFONIC ACIDS

The invention relates to a novel process for the preparation of perfluoroalkanecarboxylic acids and perfluoroalkanesulfonic acids.

Perfluoroalkanecarboxylic acids and perfluoroalkanesulfonic acids play an important role in the chemical industry of today ("Organof luorine Chemistry, Principles and Commercial Applications", R. E. Banks, B. E. Smart, J. C. Tatlow, Eds., Plenum Press, New York 1994).

Perfluoroalkanecarboxylic acids and perfluoroalkanesulfonic acids find a wide variety of uses in the chemical industry, both as synthetic intermediates and as finished products.

Long-chain perfluoroalkanecarboxylic acids and their salts are good surfactants which are able to reduce considerably the surface tension of water, of aqueous solutions and of organic liquids, even in low concentrations. These acids and their derivatives can also be used as emulsifiers, dispersing agents and foaming agents.

Short-chain perfluoroalkanesulfonic acids are used as intermediates in the preparation of sulfonamides. The latter are employed as plant growth regulators and as herbicides.

Perfluoroalkanesulfonic acids are also used as antistatic and antisoiling agents for porous substrates such as paper and textiles.

Methods for preparing perfluroalkanecarboxylic acids and perfluoroalkanesulfonic acids are already known. Thus, these acids are generally prepared either by electrochemical fluorination or by the use of chemical agents with strong oxidizing power. However, these methods each have their drawbacks.

The electrochemical fluorination technique is intricate and expensive because of the hazards associated with the use of liquid hydrogen fluoride and because of the corrosion of the electrolysis cells caused by the medium.

The oxidation routes using chemical agents comprise the action of hot oleum on perfluoroalkyl iodides. The use of oleum (very concentrated sulfuric acid containing sulfur trioxide, $SO_3$) is also hazardous on account of its corrosive properties. Furthermore, this method results in partial degradation of the carbon chain, leading to the production of a mixture of homologous fluoro acids.

The process according to the present invention uses ozone for the preparation of perfluoroalkanecarboxylic acids and perfluoroalkanesulfonic acids. Ozone allows the starting materials to be oxidized mildly and selectively, thus overcoming the drawbacks and hazards associated with the methods of the prior art.

The subject of the present invention is thus a process for the preparation of perfluoroalkanecarboxylic acids and perfluoroalkanesulfonic acids, characterized in that ozone is reacted, in a protic medium, with a perfluoroalkyl chain containing at least one oxidizable chemical group.

The perfluoroalkyl chains which thus constitute the starting materials in the context of the present invention can contain 1 to 12 carbon atoms and have the general formula $$CF_3(CF_2)_nY$$

in which Y represents the oxidizable chemical group, which can be chosen from:

compounds of formula $CF_2X$, X being a hetero atom, preferably a halogen and even more preferably iodine, or a heteroatomic group, preferably a sulfur-containing group, or an aromatic group.

According to a preferred embodiment, the sulfur-containing group is chosen from aryl thioethers, the aryl group being chosen from mono- or bicyclic radicals which can contain at least one substituent chosen from hydrogen, linear or branched alkyl radicals and halogen, ether, alkoxy, aryloxy, metal carboxylate, acyloxy, fluoroalkylthio, fluoroalkoxy and carboxylic acid radicals.

According to another preferred embodiment of the invention, the aromatic group is a mono- or bicyclic aromatic radical which can contain at least one substituent chosen from hydrogen, linear or branched alkyl radicals and halogen, ether, alkoxy, aryloxy, metal carboxylate, acyloxy, fluoroalkyl, fluoroalkoxy and carboxylic acid radicals.

In accordance with the process according to the invention, the reactions are carried out by simply placing the starting materials in contact with vapors containing ozone, which constitutes the most powerful oxidizing chemical element after fluorine, its standard oxidation potential relative to the standard hydrogen electrode being 2.07 V.

The reaction according to the present invention is carried out in protic medium. According to an advantageous embodiment, the protic medium consists of water, of alcohol or of carboxylic acids, which preferably do not contain fluorine, or mixtures thereof.

The reaction temperature is between –100° C. and 100° C., preferably between 0 and 40° C. Even more preferably, the reaction is carried out at a temperature close to room temperature.

As regards the pressure conditions, the reaction is generally carried out at a pressure below 10 bar, more preferably at a pressure close to atmospheric pressure.

In general, the process according to the invention can thus be carried out, with good efficacy under mild conditions, at room temperature and at atmospheric pressure.

According to an advantageous embodiment, the reaction according to the present invention can also be carried out in the presence of an insoluble solid product with a large specific surface area, such as, for example, silica, alumina, silica-alumina, titanium oxide, active charcoal, peats, clays and zeolites. This allows the interaction between the ozone and the perfluoro compounds to be enhanced considerably.

Given that the starting materials of formula $CF_3(CF_2)_nY$ are made very electron-poor by the fluorine atoms, it is extremely surprising and unexpected that this oxidation can take place at a temperature close to room temperature, without any particular activation.

As regards the sulfur-containing starting materials, the prior art teaches that they can only be oxidized into the corresponding sulfones with the aid of very strong reagents, such as hot chromium oxide (R. M. Scribner, J. Org. Chem, 1966, 31 3671). This conversion has no effect on the aromatic ring and does not produce polyfluoroalkanesulfonic acids. Moreover, common sulfides are oxidized with ozone into sulfoxides and then into sulfones. Thus, methyl phenyl sulfide is converted into the corresponding sulfone in quantitative yield (D. Barnard, J. Chem. Soc., 1957, 4547). It is thus particularly surprising that the oxidation with ozone, according to the invention, of arylperfluoroalkyl sulfides proceeds through to the formation of perfluoroalkanesulfonic acids, although their sulfur atom is less oxidizable than that of methyl phenyl sulfide.

Without this theory being possibly construed as limiting, it is possible that the ozone first attacks the aromatic ring rather than the sulfur atom in the starting materials comprising a sulfur-containing group.

According to a preferred embodiment of the invention, the ozone/starting material molar ratio is between 1 and 20, preferably between 2 and 5, for the perfluoroalkanecarboxylic acids, and between 3 and 8 for the perfluoroalkanesulfonic acids.

A cosolvent can advantageously be added in order to dissolve the starting material. This cosolvent can be chosen from aprotic solvents such as nitriles, in particular acetonitrile, organochlorine compounds, in particular tetrachloromethane, and secondary or tertiary amines, in particular diethylamine, triethylamine and tributylamine and amines having one or more longer alkyl chains.

The duration of the reaction according to the invention can range approximately between thirty minutes and seven days.

The aim of the examples which follow is to illustrate the invention more clearly.

EXAMPLE 1

20 g of perfluorooctyl iodide ($C_8F_{17}I$) and 150 ml of propanoic acid are introduced into a glass reactor. The mixture is stirred at room temperature and the atmosphere of the container is flushed with an ozone/oxygen mixture (6/94 volume/volume) for 2 days. The precipitate formed is then filtered off. The perfluorooctanoic acid ($C_7F_{15}COOH$) contained in the filtrate is precipitated with pentane, filtered off on a Buchner funnel and dried to give 5 g of a white solid. The yield for obtaining the perfluorooctanoic acid is thus 30%. This yield was calculated after $^{19}F$ NMR analysis in $CDCl_3$ at 300 MHz, which gives the following results:

δ (ppm) −80.9(3F, $CF_3$); −119.4(t, 2F,$CF_2$); −121.8(2F, $CF_2$); −122.2(2F,$CF_2$); −122.9(s, 2F, $CF_2$); −126.3(d, 2F, $CF_2CF_3$).

EXAMPLE 2

The process is performed as in Example 1. After reaction for twelve hours at room temperature, analysis of the residue indicates the formation of perfluorohexanoic acid ($C_5F_{11}COOH$) in a yield of 25%. This yield was calculated after $^{19}F$ NMR analysis in $CDCl_3$ at 282 MHz, which gives the following results:

δ (ppm) −80.8(t, 3F, $CF_3$); −116.5(2F, $CF_2$); −122.1(qd, 4F, 2$CF_2$); −125.7(t, 2F, $CF_2CF_3$).

EXAMPLE 3

1 g, i.e. 2.52 mmol, of tridecafluorohexylbenzene ($PhC_6F_{13}$) is mixed with 20 ml of methanol in a glass tube. The mixture is stirred at room temperature and an ozone/oxygen mixture (6/94 volume/volume) is applied to the solution for 12 hours. Analysis of the mixture indicates the formation of perfluoroheptanoic acid ($C_6F_{13}COOH$).

$^{19}F$ NMR analysis in $CDCl_3$ at 282 MHz gave the following results:

δ (ppm) −80.54 (t, 3F, $CF_3$); −116.2(d, 2F, $CF_2COOH$); −121.16(d, 2F, $CF_2$); −121.9(d, 2F, $CF_2$); −122.15(d, 2F, $CF_2$); −125.6(2F, $CF_2CF_3$).

EXAMPLE 4

0.95 g of perfluorobutyl phenyl sulfide (2.89 mmol) is mixed with 20 ml of methanol and one equivalent of triethylamine, i.e. 0.4 ml, is added. The ozone/oxygen mixture (6/94 volume/volume) is bubbled into the liquid for 7 hours. Next, a second equivalent of amine is added and the ozonolysis is continued for a further 7 hours at room temperature. A 50/50 mixture of the carboxylic acid ($C_3F_7COOH$) and of the sulfonic acid ($C_4F_9SO_3H$) is obtained.

$^{19}F$ NMR analysis in $CDCl_3$ at 282 MHz gave the following results:
$C_4F_9SO_3H$
δ (ppm) −80.6(3F, $CF_3$); −114.1(2F, $CF_2SO_3$); −120.9(2F, $CF_2$); −125.4(2F, $CF_2CF_3$).
$C_3F_7CO_2H$
δ (ppm) −80.6(3F, $CF_3$); −117.0(2F, $CF_2COOH$); −125.5 (2F, $CF_2CF_3$).

EXAMPLE 5

1 g, i.e. 5.6 mmol, of phenyl trifluoromethyl sulfide is dissolved in 20 ml of a methanol/water mixture (8/2 volume/volume). The ozone/oxygen mixture (6/94 volume/volume) is bubbled into the reaction liquid for six hours.

Analysis of the mixture indicates the formation of methyl trifluoromethanesulfonate ($CF_3SO_3Me$) and of the corresponding acid in a 3/1 ratio.

Hydrolysis of the ester is carried out in the presence of baryta for twelve hours. The excess baryta is neutralized and precipitated by adding dilute sulfuric acid until the pH is slightly acidic. The resulting trifluoromethanesulfonic acid is then precipitated using barium carbonate.

The solvents are then evaporated off and the solid is extracted continuously with acetone for six hours.

$^{19}F$ NMR analysis in $CD_3OD$ at 282 MHz gave the following results:
$CF_3SO_3H$ δ (ppm) −78.2(3F, $CF_3$)
$CF_3SO_2Me$ δ (ppm) −74.63(3F, $CF_3$)
$(CF_3SO_3)_2Ba$ δ (ppm) −78.35(3F, $CF_3$)

EXAMPLE 6

1 g, i.e. 5.6 mmol, of trifluoromethyl phenyl sulfide ($PhSCF_3$) is dissolved in 20 ml of methanol. A spatula-tip amount (5 to 10 mg) of titanium dioxide is added to the reaction mixture. The ozone-oxygen mixture (6/94 volume/volume) is bubbled into the reaction liquid for 4 hours.

The relative percentages of the products formed are evaluated by fluorine NMR. Thus, the methyl ester of trifluoromethane sulfonic acid ($CF_3SO_3H$) is present in a proportion of about 15%, and the trifluoromethanesulfonic acid is present in a proportion of about 15%.

EXAMPLE 7

1 g, i.e. 5.6 mmol, of trifluoromethyl phenyl sulfide ($PhSCF_3$) is dissolved in 20 ml of a methanolwater mixture (9/1 volume/volume). A spatula-tip amount of silica is added to the reaction mixture. The ozone/oxygen mixture (6/94 volume/volume) is bubbled into he reaction liquid for 5 h 30.

The relative percentages of the products formed re evaluated by fluorine NMR. Thus, the methyl ester of rifluoromethanesulfonic acid is present in a proportion of about 60% and trifluoromethanesulfonic acid is present in a proportion of about 30%.

What is claimed is:

1. Process for the preparation of perfluoroalkanecarboxylic acids and perfluoroalkanesulfonic acids, according to which ozone is reacted, in a protic medium, with a perfluoroalkyl chain containing at least one oxidizable chemical group selected from the group consisting of a group of formula $CF_2X$, X being a hetero atom, a heteroatomic group or an aromatic group.

2. Process according to claim 1, wherein in the group of formula $CF_2X$, X is a halogen atom.

3. Process according to claim 2, wherein X is iodine.

4. Process according to claim 1, wherein the heteroatomic group is a sulfur-containing group except for a disulfide group.

5. Process according to claim 4, wherein the sulfur-containing of group is selected from the group consisting of arylthioethers, the aryl group being chosen from mono- or bicyclic radicals which can contain at least one substituent chosen from hydrogen, linear or branched alkyl radicals and halogen, ether, alkoxy, aryloxy, metal carboxylate, acyloxy, fluoroalkylthio, fluoroalkoxy and carboxylic acid radicals.

6. Process according to claim 1, wherein the aromatic group is a mono- or bicyclic aromatic radical which can contain at least one substituent selected from the group consisting of hydrogen, linear or branched alkyl radicals and halogen, ether, alkoxy, aryloxy, metal carboxylate, acyloxy, fluoroalkyl, fluoroalkoxy and carboxylic acid radicals.

7. Process according to claim 1, wherein the protic medium is selected from the group consisting of water, alcohol, carboxylic acids, and mixtures thereof.

8. Process according to claim 7, wherein the carboxylic acids do not contain fluorine.

9. Process according to claim 1 wherein an aprotic cosolvent selected from the group consisting of nitriles, organochlorine compounds and secondary or tertiary amines, is added to the medium.

10. Process according to claim 9, wherein the aprotic cosolvent is selected from the group consisting of acetonitrile, carbon tetrachloride, diethylamine, triethylamine and tributylamine.

11. Process according to claim 1, wherein the temperature is between −100° C. and 100° C.

12. Process according to claim 11, wherein the temperature is between 0 and 40° C.

13. Process according to claim 12, wherein the temperature is close to room temperature.

14. Process according to claim 1, wherein the pressure is less than 10 bar.

15. Process according to claim 14, wherein the pressure is close to atmospheric pressure.

16. Process according to claim 1, wherein the ozone/substrate molar ratio is between 1 and 20 for the perfluoroalkanecarboxylic acids, and between 3 and 8 for the perfluoroalkanesulfonic acids.

17. Process according to claim 16, wherein the ozone/substrate molar ratio is between 2 and 5 for the perfluoroalkanecarboxylic acids.

18. Process according to claim 1, wherein an insoluble solid product selected from the group consisting of silica, alumina, silica-alumina, titanium oxide, active charcoal, peats, clays and zeolites is added.

* * * * *